US011761010B2

(12) United States Patent
Qiu et al.

(10) Patent No.: US 11,761,010 B2
(45) Date of Patent: Sep. 19, 2023

(54) SOYBEAN GENETIC TRANSFORMATION METHOD USING PMI AS SELECTABLE GENE

(71) Applicant: Institute of Crop Sciences, Chinese Academy of Agricultural Sciences, Beijing (CN)

(72) Inventors: Lijuan Qiu, Beijing (CN); Ying Wang, Beijing (CN)

(73) Assignee: Institute of Crop Sciences, Chinese Academy of Agricultural Sciences, Beijing (CN)

( * ) Notice: Subject to any disclaimer, the term of this patent is extended or adjusted under 35 U.S.C. 154(b) by 430 days.

(21) Appl. No.: 16/912,297

(22) Filed: Jun. 25, 2020

(65) Prior Publication Data
US 2020/0407736 A1    Dec. 31, 2020

(30) Foreign Application Priority Data

Jun. 25, 2019   (CN) .......................... 201910553754.2

(51) Int. Cl.
*C12N 15/82* (2006.01)
*A01H 4/00* (2006.01)

(52) U.S. Cl.
CPC ........... *C12N 15/8205* (2013.01); *A01H 4/00* (2013.01); *C12N 15/8245* (2013.01); *C12N 2500/34* (2013.01); *C12N 2500/38* (2013.01); *C12N 2500/44* (2013.01)

(58) Field of Classification Search
CPC .................................................... C12N 15/82
See application file for complete search history.

(56) References Cited

U.S. PATENT DOCUMENTS

| | | | | |
|---|---|---|---|---|
| 8,097,774 B2* | 1/2012 | Hawkes | ............. | C12N 15/8278 800/300 |
| 8,980,632 B2* | 3/2015 | Bullock | ................... | A01C 1/00 800/278 |
| 2006/0260012 A1* | 11/2006 | Khan | ................. | C12N 15/8205 800/312 |

OTHER PUBLICATIONS

Chunhong Qiu, et al., "A novel plant code optimization phosphomannose isomerase (pPMI) and its application in rice (*Oryza sativa* L.) transformation as selective marker", Plant Omics Journal, Poj 8(1):30- (2015), ISSN:1836-3644.
Heng Zhong, et al., "Advances in Agrobacterium—mediated Maize Transformation", Maize: Methods and Protocols, Methods in Molecular Biology, vol. 1676, DOI 10.1007/978-1-4939-7315-6_3.
Li Zhi, et al., "Effect of Agroliacterium strain and plasmid copy number on transformation frequency, event quality and usable event quality in an elite maize cultivar", Original Paper, Received: Oct. 24, 2014 / Revised: Dec. 17, 2014 / Accepted: Dec. 19, 2014 / Published online: Jan. 6, 2015, DOI 10.1007/s00299-014-1734-0.
M. Wright, et al., "Efficient biolistic transformation of maize (*Zea mays* L.) and wheat (*Triticum aestivum* L.) using the phosphomannose isomerase gene, pmi, as the selectable marker", Genetic Transformation and Hybridization, Received: Sep. 27, 2000 / Revision received: Nov. 3, 2000 /Accepted: Dec. 21, 2000 / Published online: Jun. 14, 2001, DOI 10.1007/s002990100318.
Seul-Hye Hur, et al., "Efficient Development of Transgenic Cabbage with Jasmonic Acid Carboxyl Methyltransferase (JMT) Gene Based on PMI / Mannose Selection System", Research Article, Received May 6, 2015; Revised Jul. 15, 2015; Accepted Jul. 24, 2015; Published Sep. 30, 2015, Online ISSN: 2287-9366.
Alessandra Pontiroli, et al., "Fate of transgenic plant DNA in the environment", Review Article, http://www.ebr-journal.org or http://dx.doi.org/10.1051/ebr:2007037, DOI: 10.1051/ebr:2007037.
Sylvia Obinda Nawiri, et al., "Genetic engineering of sweet potatoes (Ipomoea batatas) using isopentenyl transferase gene for enhanced drought tolerance", Asian Journal of Agriculture, vol. 1, No. 2, Dec. 2017, pp. 85-99, DOI: 10.13057/asianjagric/g010206.
Yuan-Yeu Yau, et al., "Less is more: strategies to remove marker genes from transgenic plants", BMC Biotechnology, 2013, pp. 1-23, http://www.biomedcentral.com/1472-6750/13/36.
Vibha Srivastava, et al., "Marker-free site-specific gene integration in plants", Trends in Biotechnology, vol. 22 No. 12, Dec. 2004, DOI:10.1016/j.tibtech.2004.10.002.
Chunhong Qiu, et al., "A novel plant code optimization phosphomannose isomerase (pPMI) and its application in rice (*Oryza Sativa* L.) transformation as selective marker", Plant Omics Journal, POJ 8(1):30-36 (2015), ISSN:1836-3644.
Lei Hu, et al., "Plant phosphomannose isomerase as a selectable marker for rice transformation", Scientific Reports, Received Feb. 3, 2016, Accepted Apr. 25, 2016, Published May 13, 2016, DOI: 10.1038/srep25921.
Brian J. Caliando, et al., "Targeted DNA degradation using a CRISPR device stably carried in the host genome", Nature Communications, Received Nov. 20, 2014, Accepted Mar. 20, 2015, Published May 19, 2015, DOI: 10.1038/ncomms7989.
Aurora Rizzi, et al., "The Stability and Degradation of Dietary DNA in the Gastrointestinal Tract of Mammals: Implications for Horizontal Gene Transfer and the Biosafety of GMOS", Taylor & Francis, Aug. 6, 2014, DOI: 10.1080/10408398.2010.499480.

(Continued)

Primary Examiner — Brent T Page
(74) Attorney, Agent, or Firm — von Briesen & Roper, s.c.

(57) ABSTRACT

The present invention provides a soybean genetic transformation method using PMI as selectable gene, and relates to the technical field of genetic engineering. In the soybean genetic transformation method of the present invention, using the PMI gene as a selectable marker, soybean explants are infected by recombinant *Agrobacterium* with the PMI gene and a target gene, followed by co-culture; without recovery culture, the co-cultured explants are directly selected by a selective medium supplemented with mannose, where transformed explants with the PMI gene grow normally under selection pressure of mannose, while non-transformed explant growth is inhibited, thereby selecting successfully transformed positive plants; after shoot elongation and transplantation of the positive plants obtained, genetically transformed soybean plants are obtained successfully. Using the soybean genetic transformation method as provided by the present invention, soybeans can be genetically transformed by PMI genes derived from any species, achieving safe soybean genetic transformation.

11 Claims, 1 Drawing Sheet

(56) References Cited

OTHER PUBLICATIONS

D. Negrotto, et al., "The use of phosphomannose-isomerase as a selectable marker to recover transgenic maize plants (*Zea mays* L.) via Agrobacterium transformation", Genetic Transformation and Hybridization, Received: Aug. 24, 1999, Revision received Sep. 27, 1999, Accepted Nov. 9, 1999.

R. L. Boscariol, et al., "The use of the PMI/mannose selection system to recover transgenic sweet orange plants (*Citrus sinensis* L. Osbeck)", Genetic Transformation and Hybridizatio, Received Nov. 29, 2003, Revised: May 2, 2003, Accepted May 5, 2003, Published online Jul. 19, 2003, DOI 10.1007/s00299-003-0654-1.

Mariam Sticklen, "Transgenic, Cisgenic, Intragenic and Subgenic Crops", Advances in Crop Science and Technology, vol. 3, Issue 2, ISSN: 2329-8863 ACST.

\* cited by examiner

ZH10　　　　Williams82

ZH688　　　　Jack

SOYBEAN GENETIC TRANSFORMATION METHOD USING PMI AS SELECTABLE GENE

CROSS-REFERENCE TO RELATED APPLICATION

This application claims priority under the Paris Convention to Chinese Patent Application No. 201910553754.2 filed on Jun. 25, 2019.

TECHNICAL FIELD

The present invention relates to the technical field of genetic engineering, and in particular to a soybean genetic transformation method using PMI as selectable gene.

BACKGROUND

Common selectable markers for plant genetic transformation are antibiotic and herbicide resistance genes, which are widely used in genetic transformation of dicotyledon and monocotyledon. However, transgene safety regulations clearly limit some antibiotics and herbicides. There are two major concerns. On one hand, because these two selective agents are somewhat toxic, their use in production may have an effect on the environment. On the other hand, when people plant transgenic crops with antibiotic resistance genes, horizontal gene transfer (Pontiroli et al., 2007; Rizzi et al., 2011) may be caused, where gene transfer to soil or other crops has influence on microflora balance in the environment and thus human health. In order to avoid selectable marker genes from putting the environment at risk, people will avoid the influence of these selectable marker genes only required during transformation on products in various ways, e.g., co-transformation and then separation, deletion of selectable gene by homologous recombination, and deletion of selectable marker gene by means of gene editing (Srivastava et al., 2004; Yau et al., 2013; Caliando et al., 2015; Sticklen et al., 2015).

However, these methods need a lot of assays, analyses, and screenings, and even extra transformation experiments, which greatly increase labor and production costs. Demand for non-antibiotic and non-herbicide selectable marker genes, e.g., 6-phosphomarmose isomerase (PMI) gene, emerges at the right moment. Mannose is harmless to plant cells but cannot be absorbed and utilized directly by plants; mannose cannot be absorbed and utilized directly by plants until it is isomerized to fructose 6-phosphate by 6-phosphomarmose isomerase. Therefore, regulation of a ratio of mannose to sucrose in a culture medium can starve non-transformed plant cells, making transformed cells grow normally.

PMI gene has been widely used in monocotyledon, such as genetic transformation of rice, corn, and wheat (Zhong et al., 2018; Wright et al., 2001; Negrotto et al., 2000; Boscariol et al., 2003; Zhi et al., 2015; Hu et al., 2016; Qiu et al., 2015). Few studies on use of the gene in dicotyledon as a selectable marker have been carried out, and transformation frequency was inconsistent. For example, the transformation frequency of potato was as high as ~50%, while that of cabbage was merely 1.2% (Nawiri et al., 2017; Hur et al., 2015). This is possibly because expression of endogenous PMI gene in some dicotyledon plants is so high that mannose can be absorbed and utilized. Particularly, in soybean genetic transformation, it is generally believed that the PMI gene cannot be used as a selectable marker.

SUMMARY

In order to overcome the defect of a PMI gene failing to serve as a selectable marker for soybean genetic transformation in the prior art, the present invention provides a soybean genetic transformation method using PMI as selectable gene, achieving safe soybean genetic transformation.

To achieve the above purpose, the present invention provides the following technical solution.

The present invention provides a soybean genetic transformation method using PMI as selectable gene, including the following steps:

(1) soaking soybean explants in a recombinant *Agrobacterium*-containing infection suspension to obtain infected explants;

a PMI gene and a target gene being present in the recombinant *Agrobacterium*;

the infection suspension, apart from the recombinant *Agrobacterium*, further including an infection medium, where the infection medium uses MS as a basic medium and further includes 1.0 to 2.0 mg/L thidiazuron;

(2) co-culturing the infected explants to obtain co-cultured explants;

(3) culturing the co-cultured explants on a selective medium directly for 18 to 25 days, to select positive plants without growth inhibition;

the selective medium using mannose as a selective agent; and (4) conducting shoot elongation and transplantation on the positive plants.

Preferably, in the step (1), the soybean explants include explants of meristem of soybean embryonic tips or soybean calluses.

Preferably, cultivars of the soybean explants include *Glycine max* 'Jack', *G. max* 'William82', *G. max* 'Zhonghuang 10', or *G. max* 'Zhonghuang 688'.

Preferably, in the step (1), the infection medium uses MS as a basic medium and further includes B5 vitamin (the B5 vitamin refers to vitamin in B5 culture medium), sucrose, thidiazuron, and 2-morpholinoethanesulfonic acid.

Preferably, in the step (1), the PMI gene comes from microbes or plants; the microbes include *Escherichia coli*; the plants include soybean, rice, or corn.

Preferably, in the step (2), a medium for the co-culture uses MS as a basic medium and further includes B5 vitamin, sucrose, 2-morpholinoethanesulfonic acid, and agar, at a pH of 5.4 to 5.8.

Preferably, conditions of the co-culture include: culture temperature 19 to 24° C., and illumination time 0 to 18 h/day.

Preferably, in the step (3), the selective medium uses B5 as a basic medium and further includes B5 vitamin, sucrose, mannose, thidiazuron, 2-morpholinoethanesulfonic acid, and agar, at a pH of 5.4 to 5.8.

Preferably, the culturing conditions in the step (3) include: culture temperature 25 to 28° C., and illumination time 14 to 18 h/day.

Preferably, in the step (4), a medium for the shoot elongation uses B5 as a basic medium and further includes B5 vitamin, sucrose, mannose, 2-morpholinoethanesulfonic acid, and agar, at a pH of 5.4 to 5.8.

Preferably, in the step (4), conditions of the shoot elongation include: culture temperature 25 to 28° C., and illumination time 14 to 18 h/day.

Compared with the Prior Art, the Beneficial Effects of the Present Invention are as Follows:

The present invention provides a soybean genetic transformation method using PMI as selectable gene. Using the PMI gene as a selectable marker, soybean explants are infected by recombinant *Agrobacterium* with the PMI gene and a target gene, followed by co-culture; without recovery culture, the co-cultured explants are directly selected by a selective medium supplemented with mannose, where transformed explants with the PMI gene grow normally under selection pressure of mannose, while non-transformed explant growth is inhibited, thereby selecting successfully transformed positive plants; after shoot elongation and transplantation of the positive plants obtained, genetically transformed soybean plants are obtained successfully. Mannose cannot be utilized by plants until it is transformed into fructose 6-phosphate by the PMI gene (6-phosphomarmose isomerase gene); expression of the PMI gene in a soybean genome is insufficient to make it use mannose in the medium to maintain cell growth. Therefore, the PMI gene cannot make cells and tissues utilize mannose to grow normally in the medium supplemented with mannose until it is overexpressed in the soybean genome. It is generally accepted that expression of the PMI gene in soybean is sufficient to support its use of mannose, so that the PMI cannot be used as the selectable marker. Breaking the traditional idea, the present invention alters transformed soybean explants and improves selection pressure and culture procedure to establish a soybean PMI selection system. Regulation of concentration of mannose in the selective medium can inhibit non-transformed cell growth and promote transformed cell regeneration. According to the soybean genetic transformation method of the present invention, transformation frequency ranges from 1.9% to 6.3% for different cultivars.

According to the soybean genetic transformation method of the present invention, soybeans can be genetically transformed by PMI genes derived from any species, having important value in environmental safety of transgenic products and soybean genetic transformation.

DETAILED DESCRIPTION

Figure 1:
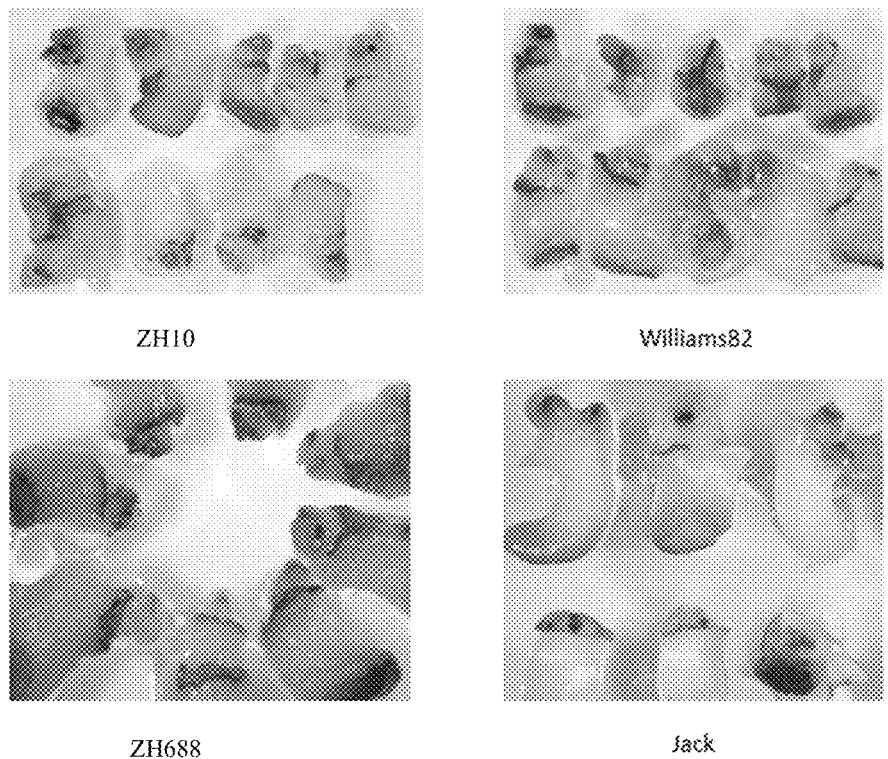
FIG. 1 illustrates GUS staining results of four better *Agrobacterium*-infected soybean cultivars in Example 9.

The present invention provides a soybean genetic transformation method using PMI as selectable gene, including the following steps:
(1) soaking soybean explants in a recombinant *Agrobacterium*-containing infection suspension to obtain infected explants;
a PMI gene and a target gene being present in the recombinant *Agrobacterium*;
the infection suspension, apart from the recombinant *Agrobacterium*, further including an infection medium, where the infection medium uses MS as a basic medium and further includes 1.0 to 2.0 mg/L thidiazuron;
(2) co-culturing the infected explants to obtain co-cultured explants;
(3) culturing the co-cultured explants on a selective medium directly for 18 to 25 days, to select positive plants without growth inhibition;
the selective medium using mannose as a selective agent and
(4) conducting shoot elongation and transplantation on the positive plants.

In the present invention, soybean explants are soaked in the recombinant *Agrobacterium* infection suspension to obtain infected explants. The recombinant *Agrobacterium* is used to transform the PMI gene and the target gene into soybean explants. *Agrobacterium* infection is conventional in the art. Unless otherwise specified, the present invention is implemented in a conventional manner.

In the present invention, the PMI gene may be derived from any species, including but not limited to microbes or plants; sources of the microbes with the PMI gene include but are not limited to *Escherichia coli*; sources of the plants with the PMI gene include but are not limited to soybean, rice, or corn.

In the present invention, a method for constructing the recombinant *Agrobacterium* preferably includes the following steps: cloning the PMI gene and the target gene into the same expression vector to construct and obtain a recombinant expression vector; introducing the recombinant expression vector into *Agrobacterium* to obtain the recombinant *Agrobacterium*. The method of the present invention is suitable for genetic transformation of any target gene and is not particularly limited to a target gene.

In the present invention, the soybean explants include but are not limited to explants of s of soybean embryonic tips or soybean calluses. In the present invention, cultivars of the soybean explants include but are not limited to *Glycine max* 'Jack', *G. max* 'William82', *G. max* 'Zhonghuang 10', or *G. max* 'Zhonghuang 688'. The soybean genetic transformation method of the present invention is appropriate for soybeans with various genotypes.

In the present invention, during the infection, the recombinant *Agrobacterium* is preferably prepared into an infection suspension with an $OD_{660}$ value of 0.6 to 1.0; more preferably, the infection suspension includes the infection medium and the recombinant *Agrobacterium*; further preferably, the infection medium uses MS as a basic medium and further includes B5 vitamin, sucrose, thidiazuron, and 2-morpholinoethanesulfonic acid; still more preferably, the infection medium includes 0.15 to 0.3 g/L basic MS medium, 2 to 10 ml/L 200×B5 vitamin, 20 to 50 g/L sucrose, 1.0 to 2.0 mg/L thidiazuron, and 0.5 to 3 g/L 2-morpholinoethanesulfonic acid, at a pH of 5.2 to 5.6. In the infection medium limited in the present invention, thidiazuron concentration can increase the transformation frequency of soybean genetic transformation significantly.

In the present invention, a method of the infection is preferably soaking, i.e., soaking soybean explants to be transformed in the recombinant *Agrobacterium*-containing infection suspension. In the present invention, the soaking temperature is preferably 25 to 28° C. In the present invention, the soaking time is preferably 0.5 to 4 h, and more preferably 1 to 2 h.

In the present invention, after the infected explants are obtained, the infected explants are co-cultured to obtain co-cultured explants. An objective of the co-culture in the present invention is to better integrate T-DNA containing the PMI gene and the target gene in *Agrobacterium* into the soybean genome.

In the present invention, the medium for the co-culture preferably uses MS as the basic medium and further includes B5 vitamin, sucrose, 2-morpholinoethanesulfonic acid, and agar, at a pH of 5.4 to 5.8; more preferably, the medium for the co-culture includes 0.15 to 0.3 g/L basic MS medium, 2 to 10 m/L 200×B5 vitamin, 20 to 50 g/L sucrose, 0.5 to 3 mg/L 2-morpholinoethanesulfonic acid, and 6 to 9 g/L agar, at a pH of 5.2 to 5.6. The basic MS medium of the present invention is a commercially available reagent, which can be used directly after weighing. In the present invention, a temperature of the co-culture is preferably 19 to 24° C., and more preferably 20 to 22° C. In the present invention, illumination time of the co-culture is preferably 0 to 18 h/day, and more preferably 14 to 16 h/day. In the present invention, the co-culturing time is preferably 4 to 5 days.

In the present invention, after the co-cultured explants are obtained, the selective medium is used to culture the co-cultured explants directly for 18 to 25 days to select positive plants without growth inhibition; the selective medium uses mannose as the selective agent. In the present invention, direct selection of the co-cultured explants can improve genetic transformation frequency when using the PMI as the selectable marker. Stress of mannose in the selective medium enables normal growth of transformed plants with selectable marker PMI gene, inhibits non-transformed plant growth, and thus selects successfully transformed positive plants.

In the present invention, the selective medium preferably uses B5 as the basic medium and further includes B5 vitamin, sucrose, mannose, thidiazuron, 2-morpholinoethanesulfonic acid, and agar, at a pH of 5.4 to 5.8; more preferably, the selective medium includes: 0.25 to 0.5 g/L basic B5 medium, 2 to 8 ml/L 200×B5 vitamin, 0 to 60 g/L sucrose, 10 to 40 g/L mannose, 0.2 to 0.3 mg/L thidiazuron, 0.5 to 2 g/L 2-morpholinoethanesulfonic acid, and 6 to 10 g/L agar, at a pH of 5.4 to 5.8; the sucrose in the selective medium is preferably 20 to 60 g/L. The basic MS medium of the present invention is a commercially available reagent, which can be used directly after weighing.

In the present invention, during the culture on the selective medium, culture temperature is preferably 25 to 28° C.; illumination time of the culture is 14 to 18 h/day, and more preferably 16 h/day; culture time is preferably 20 to 22 h/day; light intensity of the culture is preferably at least 1,500 LUX.

After the positive plants are obtained, shoot elongation and transplantation are conducted on the positive plants in the present invention. The shoot elongation and transplantation of the present invention may be conducted in the manner known in the art; the present invention preferably provides the following method for shoot elongation:

In the present invention, the medium for the shoot elongation preferably uses B5 as the basic medium and further includes B5 vitamin, sucrose, mannose, 2-morpholinoethanesulfonic acid, and agar, at a pH of 5.4 to 5.8; more preferably, the medium for the shoot elongation includes: 0.25 to 0.5 g/L basic B5 medium, 2 to 8 ml/L 200×B5 vitamin, 0 to 60 g/L sucrose, 10 to 40 g/L mannose, 0.5 to 2 g/L 2-morpholinoethanesulfonic acid, and 6 to 10 g/L agar, at a pH of 5.4 to 5.8; the sucrose in the medium for the shoot elongation preferably is 20 to 60 g/L.

In the present invention, the culture temperature of the shoot elongation is preferably 25 to 28° C. In the present invention, the illumination time of the shoot elongation is preferably 14 to 18 h/day, and more preferably 16 h/day. In the present invention, the shoot elongation time is preferably 19 to 22 days.

The technical solution provided by the present invention will be described in detail in connection with the following examples, but they should not be construed as limiting the claimed scope of the present invention.

Example 1

A genetic transformation system of soybean PMI selection was established by using *Glycine max* 'Jack' as a model recipient and a PMI gene as a screening condition.

1. Preparation of explant: Each mature seed of *G. max* 'Jack' was sterilized and then germinated on a solid medium for one day; two cotyledons and the first pair of true leaves were removed, and hypocotyl and meristem were preserved. Explants of meristems of soybean embryonic tips were obtained.

2. Preparation of infection suspension: 0.215 g of basic MS medium, 5 ml of 200×B5 vitamin, 30 g of sucrose, 1.0 mg of thidiazuron, and 1 g of 2-morpholinoethanesulfonic acid were dissolved in 1 L of water, and adjusted to pH 5.4 to obtain an infection medium.

Vector construction: An expression vector was constructed by using a binary vector pCAMBIA3301 as a basic transformation vector. EcoliPMI sequence (as shown in SEQ ID NO. 1) of *Escherichia coli* obtained on NCBI website was synthesized into a gene fragment and cloned into the binary vector pCAMBIA3301 to obtain a recombinant expression vector. There were two expression elements in the recombinant expression vector: one was a GUS expression element used for transient expression assay, i.e., pr35S-GUS-tNOS; the other was a selectable marker gene used for selection, i.e., pr35S-EcoliPMI-tNOS. The binary vector was introduced into *Agrobacterium* EHA101 by electroporation; after correct verification, recombinant *Agrobacterium* was obtained and stored in a refrigerator at −80° C. for use.

After culture, the recombinant *Agrobacterium* was dissolved in the infection medium; an infection suspension was obtained once $OD_{660}$ was measured to be 0.6.

3. Infection and co-culture: Explants of meristems of soybean embryonic tips were soaked in the infection suspension for 2 h; infected explants were removed, placed onto the surface of a co-culture medium or a piece of filter paper supplemented with 1 mL of liquid co-culture medium, and cultured in the dark at 23° C. for 5 days.

The co-culture medium was prepared as follows: 0.215 g of basic MS medium, 5 ml of 200×B5 vitamin, 30 g of sucrose, 1 g of 2-morpholinoethanesulfonic acid, and 7.5 g of agar were dissolved in 1 L of water, and adjusted to pH 5.6.

The liquid co-culture medium was prepared as follows: 0.215 g of basic MS medium, 5 ml of 200×B5 vitamin, 30 g of sucrose, and 1 g of 2-morpholinoethanesulfonic acid were dissolved in 1 L of water, and adjusted to pH 5.6.

4. Selective culture: The co-cultured explants were transferred onto a selective medium supplemented with mannose and cultured for three weeks at 25° C.; explants grown normally were selected as positive plants. The culture was on a 16 h light/8 h dark cycle. Light intensity was above 1,500 LUX.

The selective medium was prepared as follows: 0.31 g of basic B5 medium, 5 ml of 200×B5 vitamin, 5 g of sucrose, 20 g of mannose, 0.2 mg of thidiazuron, 1 g of 2-morpholinoethanesulfonic acid, and 7.5 g of agar were dissolved in 1 L of water, and adjusted to pH 5.6.

5. Shoot elongation: The selected positive plants were transferred onto a shoot elongation medium and kept culturing for three weeks to obtain elongated plants.

Culture conditions were as follows: light culture at 25° C., on a 16 h light/8 h dark cycle. The light intensity was above 1,500 LUX.

The shoot elongation medium included: 0.31 g of basic B5 medium, 5 ml of 200×B5 vitamin, 5 g of sucrose, 20 g of mannose, 1 g of 2-morpholinoethanesulfonic acid, and 7.5 g of agar, at a pH of 5.6.

6. Transplantation and identification by staining: The elongated plants were identified by GUS staining; the stained elongated plants were directly transplanted in a culture matrix without rooting. The transplanted plants were watered and moisturized in plastic bags; one week later, plastic bags were removed and the plants were managed normally.

The culture matrix was a mixture of turfy soil and vermiculite in a volume ratio of 1:1. Culture conditions were: 28° C., a 16 h light/8 h dark cycle.

Comparative Example 1

A genetic transformation system of soybean PMI selection was established by using *Glycine max* 'Jack' and *G. max* 'Zhonghuang 688' as model recipients and a PMI gene as a screening condition.

1. Preparation of explant: Each mature seed of *G. max* 'Jack' was sterilized and then germinated on a solid medium for one day; two cotyledons and the first pair of true leaves were removed, and hypocotyl with meristem were preserved. Explants of meristem soybean embryonic tips were obtained.

2. Preparation of infection suspension: 0.215 g of basic MS medium, 5 ml of 200×B5 vitamin, 30 g of sucrose, 1.0 mg of thidiazuron, and 1 g of 2-morpholinoethanesulfonic acid were dissolved in 1 L of water, and adjusted to pH 5.4 to obtain an infection medium.

Vector construction: An expression vector was constructed by using a binary vector pCAMBIA3301 as a basic transformation vector. EcoliPMI sequence (as shown in SEQ ID NO. 1) of *Escherichia coli* obtained on NCBI website was synthesized into a gene fragment and cloned into the binary vector pCAMBIA3301 to obtain a recombinant expression vector. There were two expression elements in the recombinant expression vector: one was a GUS expression element used for transient expression assay, i.e., pr35S-GUS-tNOS; the other was a selectable marker gene used for selection, i.e., pr35S-EcoliPMI-tNOS. The binary vector was introduced into *Agrobacterium* EHA101 by electroporation; after correct verification, recombinant *Agrobacterium* was obtained and stored in a refrigerator at −80° C. for use.

After culture, the recombinant *Agrobacterium* was dissolved in the infection medium; an infection suspension was obtained once $OD_{660}$ was measured to be 0.6.

3. Infection and co-culture: Explants of s of soybean embryonic tips were soaked in the infection suspension for 2 h; infected explants were removed, placed onto the surface of a co-culture medium or a piece of filter paper supplemented with 1 mL of liquid co-culture medium, and cultured in the dark at 23° C. for 5 days.

The co-culture medium was prepared as follows: 0.215 g of basic MS medium, 5 ml of 200×B5 vitamin, 30 g of sucrose, 1 g of 2-morpholinoethanesulfonic acid, and 7.5 g of agar were dissolved in 1 L of water, and adjusted to pH 5.6.

The liquid co-culture medium was prepared as follows: 0.215 g of basic MS medium, 5 ml of 200×B5 vitamin, 30 g of sucrose, and 1 g of 2-morpholinoethanesulfonic acid were dissolved in 1 L of water, and adjusted to pH 5.6.

4. Recovery culture: The co-cultured explants were transferred onto a recovery medium without mannose and cultured for seven days at 25° C. The culture was on a 16 h light/8 h dark cycle. Light intensity was above 1,500 LUX.

The recovery medium was prepared as follows: 0.31 g of basic B5 medium, 5 ml of 200×B5 vitamin, 30 g of sucrose, 0.2 mg of thidiazuron, 1 g of 2-morpholinoethanesulfonic acid, and 7.5 g of agar were dissolved in 1 L of water, and adjusted to pH 5.6.

5. Selective culture: The explants after recovery culture were transferred onto a selective medium supplemented with mannose and cultured for three weeks at 25° C.; explants grown normally were selected as positive plants. The culture was on a 16 h light/8 h dark cycle. The light intensity was above 1,500 LUX.

The selective medium was prepared as follows: 0.31 g of basic B5 medium, 5 ml of 200×B5 vitamin, 5 g of sucrose, 20 g of mannose, 0.2 mg of thidiazuron, 1 g of 2-morpholinoethanesulfonic acid, and 7.5 g of agar were dissolved in 1 L of water, and adjusted to pH 5.6.

6. Shoot elongation: The selected positive plants were transferred onto a shoot elongation medium and kept culturing for three weeks to obtain elongated plants. Culture conditions were as follows: light culture at 25° C., on a 16 h light/8 h dark cycle. The light intensity was above 1,500 LUX.

The shoot elongation medium included: 0.31 g of basic B5 medium, 5 ml of 200×B5 vitamin, 5 g of sucrose, 20 g of mannose, 1 g of 2-morpholinoethanesulfonic acid, and 7.5 g of agar, at a pH of 5.6.

7. Transplantation and identification by staining: The elongated plants were identified by GUS staining; the stained elongated plants were directly transplanted in a culture matrix without rooting. The transplanted plants were watered and moisturized in plastic bags; one week later, plastic bags were removed and the plants were managed normally.

The culture matrix was a mixture of turfy soil and vermiculite in a volume ratio of 1:1. Culture conditions were: 28° C., a 16 h light/8 h dark cycle.

The difference between Example 1 and Comparative Example 1 was that: in Comparative Example 1, the culture was conducted on the recovery medium for seven days after co-culture, but in Example 1, the explants were transferred to the selective medium directly after co-culture. Transformation frequencies of Example 1 and Comparative Example 1 were calculated, respectively (transformation frequency=number of positive plants/number of explants× 100%).

Results are listed in Table 1. The transformation frequency of the method as described in Example 1 is 3.1%, whereas that of the method as described in Comparative Example 1 is merely 0.5%, indicating that the transformation frequency of recovery culture after co-culture is significantly lower than that without recovery culture. That is, the method as provided by the present invention can significantly improve the soybean genetic transformation frequency when using the PMI gene as a selectable marker.

TABLE 1

Transformation frequencies of different recovery cultures

| Group | Selection method | Recipient cultivar | Selectable marker | Number of explants (explant) | Number of transgenic positive plants (plant) | Transformation frequency % |
|---|---|---|---|---|---|---|
| Comparative Example 1 | Recovery for 7 days | Jack | PMI | 436 | 2 | 0.5 |
| Example 1 | No recovery | Jack | PMI | 415 | 13 | 3.1 |

Example 2

1. Preparation of explant: Each mature seed of *Glycine max* 'Jack' was sterilized and then germinated on a solid medium for one day: two cotyledons and the first pair of true leaves were removed, and hypocotyl and meristem were preserved. Thirty-eight explants of meristems of soybean embryonic tips were obtained.
2. Preparation of infection suspension: 0.2 g of basic MS medium, 4 ml of 200×B5 vitamin, 30 g of sucrose, 1.2 mg of thidiazuron, and 1.5 g of 2-morpholinoethanesulfonic acid were dissolved in 1 L of water, and adjusted to pH 5.4 to obtain an infection medium.

Vector construction: An expression vector was constructed by using a binary vector pCAMBIA3301 as a basic transformation vector. EcoliPMI sequence (as shown in SEQ ID NO. 1) of *Escherichia coli* obtained on NCBI website was synthesized into a gene fragment and cloned into the binary vector pCAMBIA3301 to obtain a recombinant expression vector. There were two expression elements in the recombinant expression vector: one was a GUS expression element used for transient expression assay, i.e., pr35S-GUS-tNOS; the other was a selectable marker gene used for selection, i.e., pr35S-EcoliPMI-tNOS. The binary vector was introduced into *Agrobacterium* EHA101 by electroporation; after correct verification, recombinant *Agrobacterium* was obtained and stored in a refrigerator at −80° C. for use.

After culture, the recombinant *Agrobacterium* was dissolved in the infection medium; an infection suspension was obtained once $OD_{660}$ was measured to be 0.8.

3. Infection and co-culture: Explants of meristems of soybean embryonic tips were soaked in the infection suspension for 4 h; infected explants were removed, placed onto the surface of a co-culture medium or a piece of filter paper supplemented with 1 mL of liquid co-culture medium, and cultured in the dark at 23° C. for 4 days.

The co-culture medium was prepared as follows: 0.2 g of basic MS medium, 5 ml of 200×B5 vitamin, 35 g of sucrose, 1 g of 2-morpholinoethanesulfonic acid, and 7 g of agar were dissolved in 1 L of water, and adjusted to pH 5.6.

The liquid co-culture medium was prepared as follows: 0.2 g of basic MS medium, 5 ml of 200×B5 vitamin, 40 g of sucrose, and 1 g of 2-morpholinoethanesulfonic acid were dissolved in 1 L of water, and adjusted to pH 5.6.

4. Selective culture: The co-cultured explants were transferred onto a selective medium supplemented with mannose and cultured for three weeks at 26° C.; explants grown normally were selected as positive plants. The culture was on a 14 h light/10 h dark cycle. Light intensity was above 1,500 LUX.

The selective medium was prepared as follows: 0.31 g of basic B5 medium, 5 ml of 200×B5 vitamin, 5 g of sucrose, 20 g of mannose, 0.2 mg of thidiazuron, 1 g of 2-morpholinoethanesulfonic acid, and 7.5 g of agar were dissolved in 1 L of water, and adjusted to pH 5.6.

5. Shoot elongation: The selected positive plants were transferred onto a shoot elongation medium and kept culturing for three weeks to obtain elongated plants. Culture conditions were as follows: light culture at 27° C., on a 18 h light/6 h dark cycle. The light intensity was above 1,500 LUX.

The shoot elongation medium included: 0.31 g of basic B5 medium, 5 ml of 200×B5 vitamin, 5 g of sucrose, 20 g of mannose, 1 g of 2-morpholinoethanesulfonic acid, and 7.5 g of agar, at a pH of 5.6.

6. Transplantation and identification by staining: The elongated plants were identified by GUS staining; the stained elongated plants were directly transplanted in a culture matrix without rooting. The transplanted plants were watered and moisturized in plastic bags; one week later, plastic bags were removed and the plants were managed normally.

The culture matrix was a mixture of turfy soil and vermiculite in a volume ratio of 1:1. Culture conditions were: 28° C., a 16 h light/8 h dark cycle.

Example 3

The remaining steps were the same as those in Example 2 except that 45 explants of meristems of soybean embryonic tips were prepared and obtained and that mannose content was 15 g/L and sucrose content was 10 g/L in the selective medium.

Example 4

The remaining steps were the same as those in Example 2 except that 46 explants of meristems of soybean embryonic tips were prepared and obtained and that mannose content was 5 g/L and sucrose content was 25 g/L in the selective medium.

Example 5

The remaining steps were the same as those in Example 2 except that 53 explants of meristems of soybean embryonic tips were prepared and obtained and that mannose content was 15 g/L and sucrose content was 7.5 g/L in the selective medium.

Example 6

The remaining steps were the same as those in Example 2 except that sources of soybean seeds used were different from those of Example 2 and that 204 explants of meristems of soybean embryonic tips were prepared and obtained.

Example 7

The remaining steps were the same as Example 4 except that sources of soybean seeds used were different from those of Example 4 and that 62 explants of meristems of soybean embryonic tips were prepared and obtained.

Numbers of regenerated plants, explants, and GUS-positive plants according to the methods of Examples 2 to 7 were counted, and regeneration and transformation frequencies were calculated, where regeneration frequency=(number of regenerated plants(only one regenerated plant was calculated for each explant)/number of explants)× 100%;

transformation frequency (TF)=(number of GUS-positive plants/number of explants)×100%.

Results are listed in Table 2. Soybean genetic transformation can be achieved at all concentrations of four selective media limited in the present invention. Particularly, a combination of "20 g of mannose and 5 g of sucrose" is most applicable for PMI selection of *Glycine max* 'Jack' transformation, and transformation frequencies thereof are 5.3% and 4.4%, higher than those obtained by other treatments.

TABLE 2

Transformation frequencies at concentrations of mannitol and sucrose in different selective media

| Group | Soybean cultivar | Concentrations of mannose and sucrose in the selective medium (g/L) | Number of explants (explant) | Number of regenerated plants (plant) | Number of GUS-positive plants (plant) | Regeneration frequency (%) | Transformation frequency (%) |
|---|---|---|---|---|---|---|---|
| Example 2 | Jack | 20 + 5 | 38 | 5 | 2 | 13.2% | 5.3% |
| Example 3 | Jack | 15 + 10 | 45 | 7 | 1 | 15.6% | 2.2% |
| Example 4 | Jack | 5 + 25 | 46 | 9 | 1 | 19.6% | 2.2% |
| Example 6 | Jack | 20 + 5 | 204 | 121 | 9 | 59.3% | 4.4% |
| Example 5 | Jack | 15 + 7.5 | 53 | 42 | 2 | 79.2% | 3.8% |
| Example 7 | Jack | 5 + 25 | 62 | 50 | 1 | 80.6% | 1.6% |

Example 8

A genetic transformation system of soybean PMI selection was established by using *Glycine max* 'Jack' and *G. max* 'Zhonghuang 688' as model recipients and a PMI gene as a screening condition.

1. Preparation of explant: Each mature seed of *G. max* 'Jack' was sterilized and then germinated on a solid medium for one day; two cotyledons and the first pair of true leaves were removed, and hypocotyl and meristem were preserved. Explants of meristems of soybean embryonic tips were obtained.
2. Preparation of infection suspension: 0.215 g of basic MS medium, 5 ml of 200×B5 vitamin, 30 g of sucrose, 1.0 mg of thidiazuron, and 1 g of 2-morpholinoethanesulfonic acid were dissolved in 1 L of water, and adjusted to pH 5.5 to obtain an infection medium.

Vector construction: An expression vector was constructed by using a binary vector pCAMBIA3301 as a basic transformation vector. EcoliPMI sequence (as shown in SEQ ID NO. 1) of *Escherichia coli* obtained on NCBI website was synthesized into a gene fragment and cloned into the binary vector pCAMBIA3301 to obtain a recombinant expression vector. There were two expression elements in the recombinant expression vector: one was a GUS expression element used for transient expression assay, i.e., pr35S-GUS-tNOS; the other was a selectable marker gene used for selection, i.e., pr35S-EcoliPMI-tNOS. The binary vector was introduced into *Agrobacterium* EHA101 by electroporation; after correct verification, recombinant *Agrobacterium* was obtained and stored in a refrigerator at −80° C. for use.

After culture, the recombinant *Agrobacterium* was dissolved in the infection medium; an infection suspension was obtained once $OD_{660}$ was measured to be 0.8.

3. Infection and co-culture: Explants of meristems of soybean embryonic tips were soaked in the infection suspension for 0.5 h; infected explants were removed, placed onto the surface of a co-culture medium or a piece of filter paper supplemented with 1 mL of liquid co-culture medium, and cultured in the dark at 23° C. for 4 days.

The co-culture medium was prepared as follows: 0.215 g of basic MS medium, 5 ml of 200×B5 vitamin, 30 g of sucrose, 1 g of 2-morpholinoethanesulfonic acid, and 7.5 g of agar were dissolved in 1 L of water, and adjusted to pH 5.5.

The liquid co-culture medium was prepared as follows: 0.215 g of basic MS medium, 6 ml of 200×B5 vitamin, 25 g of sucrose, and 1 g of 2-morpholinoethanesulfonic acid were dissolved in 1 L of water, and adjusted to pH 5.5.

4. Selective culture: The co-cultured explants were transferred onto a selective medium supplemented with mannose and cultured for three weeks at 25° C.; explants grown normally were selected as positive plants. The culture was on a 16 h light/8 h dark cycle. Light intensity was above 1,500 LUX.

The selective medium was prepared as follows: 0.31 g of basic B5 medium, 6 ml of 200×B5 vitamin, 5 g of sucrose, 22 g of mannose, 0.2 mg of thidiazuron, 1 g of 2-morpholinoethanesulfonic acid, and 7.5 g of agar were dissolved in 1 L of water, and adjusted to pH 5.6.

5. Shoot elongation: The selected positive plants were transferred onto a shoot elongation medium and kept culturing for three weeks to obtain elongated plants. Culture conditions were as follows: light culture at 25° C., on a 16 h light/8 h dark cycle. The light intensity was above 1,500 LUX.

The shoot elongation medium included: 0.31 g of basic B5 medium, 5 ml of 200×B5 vitamin, 5 g of sucrose, 20 g of mannose, 1 g of 2-morpholinoethanesulfonic acid, and 7.5 g of agar, at a pH of 5.5.

6. Transplantation and identification by staining: The elongated plants were identified by GUS staining; the stained elongated plants were directly transplanted in a culture matrix without rooting. The transplanted plants were watered and moisturized in plastic bags; one week later, plastic bags were removed and the plants were managed normally.

The culture matrix was a mixture of turfy soil and vermiculite in a volume ratio of 1:1. Culture conditions were: 28° C., a 16 h light/8 h dark cycle.

Example 9

The remaining steps were the same as those in Example 1 except that thidiazuron content was 2.0 mg/L in the infection medium.

Comparative Example 2

The remaining steps were the same as those in Example 1 except that thidiazuron content was 0.5 mg/L in the infection medium.

Numbers of regenerated plants and GUS-positive plants, regeneration and transformation frequencies according to the methods of Examples 8 to 9 and Comparative Example 2 were calculated, respectively.

Results are shown in Table 3. Thidiazuron (TDZ) can be used in the selective medium to increase regeneration and transformation frequencies when TDZ concentrations are 1 mg/L and 2 mg/L, and there is little difference between both concentrations. However, 0.5 mg/L TDZ cannot obtain transgenic positive plants.

TABLE 3

Transformation frequencies at different concentrations of TDZ in the infection medium

| Group | Cultivar | Concentration of TDZ in the infection medium (mg/L) | Number of explants (explants) | Number of regenerated plants (plant) | Number of PMI-positive plants (plant) | Regeneration frequency (%) | Transformation frequency (%) |
|---|---|---|---|---|---|---|---|
| Comparative Example 2 | Jack | 0.5 | 65 | 25 | 0 | 38.5% | 0.0% |
| Example 8 | Jack | 1 | 54 | 13 | 1 | 24.1% | 1.9% |
| Example 9 | Jack | 2 | 63 | 26 | 1 | 41.3% | 1.6% |

Example 10

A genetic transformation system of soybean PMI selection was established by using *Glycine max* 'Zhonghuang 688' (ZH688) as a model recipient and a PMI gene as a screening condition.

1. Preparation of explant: Each mature seed of *G. max* 'Zhonghuang 688' was sterilized and then germinated on a solid medium for one day; two cotyledons and the first pair of true leaves were removed, and hypocotyl and meristem were preserved. Explants of meristems of soybean embryonic tips were obtained.
2. Preparation of infection suspension: 0.215 g of basic MS medium, 5 ml of 200×B5 vitamin, 30 g of sucrose, 1.0 mg of thidiazuron, and 1 g of 2-morpholinoethanesulfonic acid were dissolved in 1 L of water, and adjusted to pH 5.4 to obtain an infection medium.

Vector construction: An expression vector was constructed by using a binary vector pCAMBIA3301 as a basic transformation vector. EcoliPMI sequence (as shown in SEQ ID NO. 1) of *Escherichia coli* obtained on NCBI website was synthesized into a gene fragment and cloned into the binary vector pCAMBIA3301 to obtain a recombinant expression vector. There were two expression elements in the recombinant expression vector: one was a GUS expression element used for transient expression assay, i.e., pr35S-GUS-tNOS; the other was a selectable marker gene used for selection, i.e., pr35S-EcoliPMI-tNOS. The binary vector was introduced into *Agrobacterium* EHA101 by electroporation; after correct verification, recombinant *Agrobacterium* was obtained and stored in a refrigerator at −80° C. for use.

After culture, the recombinant *Agrobacterium* was dissolved in the infection medium; an infection suspension was obtained once $OD_{660}$ was measured to be 0.6.

3. Infection and co-culture: Explants of meristems of soybean embryonic tips were soaked in the infection suspension for 2 h; infected explants were removed, placed onto the surface of a co-culture medium or a piece of filter paper supplemented with 1 mL of liquid co-culture medium, and cultured in the dark at 23° C. for 5 days.

The co-culture medium was prepared as follows: 0.215 g of basic MS medium, 5 ml of 200×B5 vitamin, 30 g of sucrose, 1 g of 2-morpholinoethanesulfonic acid, and 7.5 g of agar were dissolved in 1 L of water, and adjusted to pH 5.6.

The liquid co-culture medium was prepared as follows: 0.215 g of basic MS medium, 5 ml of 200×B5 vitamin, 30 g of sucrose, and 1 g of 2-morpholinoethanesulfonic acid were dissolved in 1 L of water, and adjusted to pH 5.6.

4. Selective culture: The co-cultured explants were transferred onto a selective medium supplemented with mannose and cultured for three weeks at 25° C.; explants grown normally were selected as positive plants. The culture was on a 16 h light/8 h dark cycle. Light intensity was above 1,500 LUX.

The selective medium was prepared as follows: 0.31 g of basic B5 medium, 5 ml of 200×B5 vitamin, 5 g of sucrose, 20 g of mannose, 0.2 mg of thidiazuron, 1 g of 2-morpholinoethanesulfonic acid, and 7.5 g of agar were dissolved in 1 L of water, and adjusted to pH 5.6.

5. Shoot elongation: The selected positive plants were transferred onto a shoot elongation medium and kept culturing for three weeks to obtain elongated plants. Culture conditions were as follows: light culture at 25° C., on a 16 h light/8 h dark cycle. The light intensity was above 1,500 LUX.

The shoot elongation medium included: 0.31 g of basic B5 medium, 5 ml of 200×B5 vitamin, 5 g of sucrose, 20 g of mannose, 1 g of 2-morpholinoethanesulfonic acid, and 7.5 g of agar, at a pH of 5.6.

6. Transplantation and identification by staining: The elongated plants were identified by GUS staining; the stained elongated plants were directly transplanted in a culture matrix without rooting. The transplanted plants were watered and moisturized in plastic bags; one week later, plastic bags were removed and the plants were managed normally.

The culture matrix was a mixture of turfy soil and vermiculite in a volume ratio of 1:1. Culture conditions were: 28° C., a 16 h light/8 h dark cycle.

Comparative Example 3

The remaining steps were identical except that thidiazuron (TDZ) concentration was 0.1 mg/L in the selective medium.

Numbers of regenerated plants and GUS-positive plants, regeneration and transformation frequencies according to the methods of Example 10 and Comparative Example 3 were calculated, respectively.

Results are listed in Table 4. There is little difference in regeneration frequency obtained when the selective medium is supplemented with two concentrations of TDZ, but there is a significant difference in transformation frequency, i.e., 1.2% and 6.3%, respectively.

TABLE 4

Transformation frequencies at different concentrations of TDZ in the infection medium

| Group | Cultivar | Concentration of TDZ in the infection medium (mg/L) | Number of explants (explants) | Number of regenerated plants (plant) | Number of PMI-positive plants (plant) | Regeneration frequency (%) | Transformation frequency (%) |
|---|---|---|---|---|---|---|---|
| Comparative Example 3 | ZH688 | 0.1 | 82 | 48 | 1 | 58.5% | 1.2% |
| Example 10 | ZH688 | 0.2 | 80 | 44 | 5 | 55.0% | 6.3% |

Example 11

Genetic transformation was conducted by using *Escherichia coli*-derived PMI gene as a selectable marker and explants of *Glycine max* 'Jack', *G. max* 'Williams82', *G. max* 'Zhonghuang 10' (ZH10), *G. max* 'Zhonghuang 37' (ZH37), *G. max* 'Heihe No. 45' (HH45), *G. max* 'Jinyuan 55' (JY55), and *G. max* 'Zhonghuang 688' (ZH688) as recipients:

1. Preparation of explant: Mature seeds of *G. max* 'Jack', *G. max* 'Williams82', *G. max* 'Zhonghuang 10', *G. max* 'Zhonghuang 37', *G. max* 'Heihe No. 45', *G. max* 'Jinyuan 55', and *G. max* 'Zhonghuang 688' were sterilized and then germinated on a solid medium for one day; for each seed, two cotyledons and the first pair of true leaves were removed, and hypocotyl and meristem were preserved. Explants of meristems of soybean embryonic tips of *G. max* 'Jack', *G. max* 'Williams82', *G. max* 'Zhonghuang 10'. *G. max* 'Zhonghuang 37', *G. max* 'Heihe No. 45', *G. max* 'Jinyuan 55', and *G. max* 'Zhonghuang 688' were obtained.

2. Preparation of infection suspension: 0.215 g of basic MS medium, 5 ml of 200×B5 vitamin, 30 g of sucrose, 1.0 mg of thidiazuron, and 1 g of 2-morpholinoethanesulfonic acid were dissolved in 1 L of water, and adjusted to pH 5.4 to obtain an infection medium.

Vector construction: An expression vector was constructed by using a binary vector pCAMBIA3301 as a basic transformation vector. EcoliPMI sequence (as shown in SEQ ID NO. 1) of *Escherichia coli* obtained on NCBI website was synthesized into a gene fragment and cloned into the binary vector pCAMBIA3301 to obtain a recombinant expression vector. There were two expression elements in the recombinant expression vector: one was a GUS expression element used for transient expression assay, i.e., pr35S-GUS-tNOS; the other was a selectable marker gene used for selection, i.e., pr35S-EcoliPMI-tNOS. The binary vector was introduced into *Agrobacterium* EHA101 by electroporation; after correct verification, recombinant *Agrobacterium* was obtained and stored in a refrigerator at −80° C. for use.

After culture, the recombinant *Agrobacterium* was dissolved in the infection medium; an infection suspension was obtained once $OD_{660}$ was measured to be 0.6.

3. Infection and co-culture: Explants of meristems of soybean embryonic tips were soaked in the infection suspension for 2 h; infected explants were removed, placed onto the surface of a co-culture medium or a piece of filter paper supplemented with 1 mL of liquid co-culture medium, and cultured in the dark at 23° C. for 5 days.

The co-culture medium was prepared as follows: 0.215 g of basic MS medium, 5 ml of 200×B5 vitamin, 30 g of sucrose, 1 g of 2-morpholinoethanesulfonic acid, and 7.5 g of agar were dissolved in 1 L of water, and adjusted to pH 5.6.

The liquid co-culture medium was prepared as follows: 0.215 g of basic MS medium, 5 ml of 200×B5 vitamin, 30 g of sucrose, and g of 2-morpholinoethanesulfonic acid were dissolved in 1 L of water, and adjusted to pH 5.6.

Transient expression assay for *Agrobacterium* infection: Some of the co-cultured explants were placed in a GUS staining solution to stain for 12 h, and then destained with 70% alcohol; number of stained explants and staining intensity were calculated. GUS-positive rate (GUS-positive rate=number of stained explants/total number of stained explants×100%) was calculated.

4. Selective culture: The co-cultured explants were transferred onto a selective medium supplemented with mannose and cultured for three weeks at 25° C.; explants grown normally were selected as positive plants. The culture was on a 16 h light/8 h dark cycle. Light intensity was above 1,500 LUX.

The selective medium was prepared as follows: 0.31 g of basic B5 medium, 5 ml of 200×B5 vitamin, 5 g of sucrose, 20 g of mannose, 0.2 mg of thidiazuron, 1 g of 2-morpholinoethanesulfonic acid, and 7.5 g of agar were dissolved in 1 L of water, and adjusted to pH 5.6.

5. Shoot elongation: The selected positive plants were transferred onto a shoot elongation medium and kept culturing for three weeks to obtain elongated plants. Culture conditions were as follows: light culture at 25° C., on a 16 h light/8 h dark cycle. The light intensity was above 1,500 LUX.

The shoot elongation medium included: 0.31 g of basic B5 medium, 5 ml of 200×B5 vitamin, 5 g of sucrose, 20 g of mannose, 1 g of 2-morpholinoethanesulfonic acid, and 7.5 g of agar, at a pH of 5.6.

6. Transplantation and identification by staining: The elongated plants were identified by GUS staining; the stained elongated plants were directly transplanted in a culture matrix without rooting. The transplanted plants were watered and moisturized in plastic bags; one week later, plastic bags were removed and the plants were managed normally.

The culture matrix was a mixture of turfy soil and vermiculite in a volume ratio of 1:1. Culture conditions were: 28° C., a 16 h light/8 h dark cycle.

Identification by GUS staining: Leaves of elongated plants were placed in a GUS staining solution and allowed to stand for 12 h at 37° C. Leaves were removed and destained with 70% alcohol, and then leaf color was observed. Blue-stained leaves were transgenic positive plants.

Preparation of GUS staining solution was as follows: 25 ml of 1 M sodium phosphate (Na$_2$PO$_4$), 5 ml of 500 mM sodium ethylenediamine tetracetate (EDTA), and 125 mg of 5-bromo-4-chloro-3-indolyl β-D-glucoside (X-Glu) were dissolved in water, and the solution was adjusted to pH 8.0.

*G. max* 'Jack', *G. max* 'Williams82', *G. max* 'Zhonghuang 10' (ZH10), *G. max* 'Zhonghuang 37' (ZH37), *G. max* 'Heihe No. 45' (HH45), *G. max* 'Jinyuan 55' (JY55), and *G. max* 'Zhonghuang 688' (ZH688) were subject to *Agrobacterium* infection and co-culture. GUS staining results of the co-cultured explants showed that *G. max* 'Jack', *G. max* 'Williams82', *G. max* 'Zhonghuang 10', *G. max* 'Heihe No. 45', and *G. max* 'Zhonghuang 688' could be infected by *Agrobacterium* and stained (Table 5). However, *G. max* 'Jack', *G. max* 'Williams82', *G. max* 'Zhonghuang 10', and *G. max* 'Zhonghuang 688' showed better infection effects. FIG. 1 illustrates transient expression staining of the four cultivars.

TABLE 5

Transient expression results of *Agrobacterium* infection of different cultivars

| Cultivar | Number of explants | Number of GUS-positive explants (explant) | Number of heavily stained explants (explant) | Number of moderately stained explants (explant) | Number of slightly stained explants (explant) | GUS-positive rate (%) |
|---|---|---|---|---|---|---|
| Jack | 47 | 23 | 12 | 7 | 3 | 49% |
| williams 82 | 43 | 10 | 4 | 4 | 2 | 23% |
| ZH10 | 38 | 9 | 3 | 3 | 3 | 24% |
| ZH37 | 42 | 0 | 0 | 0 | 0 | 0% |
| HH45 | 41 | 6 | 0 | 0 | 6 | 15% |
| JY55 | 36 | 0 | 0 | 0 | 0 | 0% |
| ZH688 | 37 | 8 | 4 | 2 | 2 | 22% |

Example 12

According to the method as described in Example 11, *Glycine max* 'Jack', *G. max* 'Williams82', *G. max* 'Zhonghuang 10' (ZH10), and *G. max* 'Zhonghuang 688' (ZH688) were subject to three runs of transformation tests using *Escherichia coli*-derived *E. coli* PMI as a selectable marker; numbers of explants and positive plants were counted and transformation frequency (transformation frequency=number of positive plants/number of explants× 100%) was calculated during each run of the test.

Figure 2:
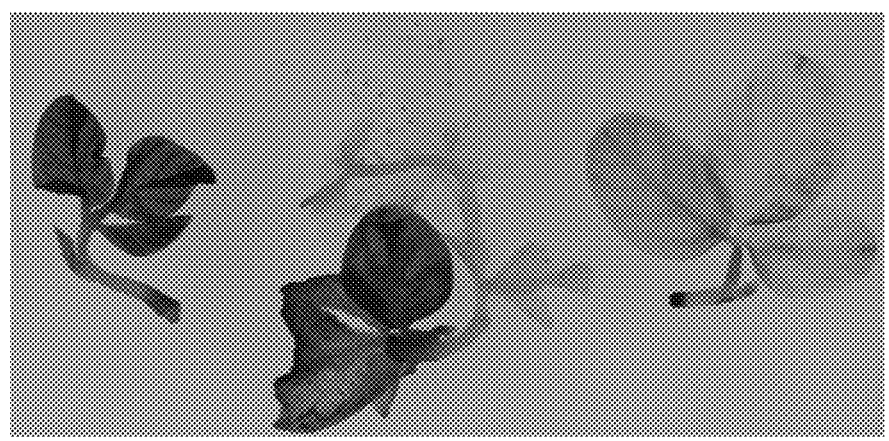
FIG. 2 illustrates a GUS staining result of *Glycine max* 'Jack' transformant in Example 10.

Statistical results are listed in Table 6. Transformation frequencies of *G. max* 'Jack', *G. max* 'Williams82', *G. max* 'Zhonghuang 10' (ZH10), and *G. max* 'Zhonghuang 688' (ZH688) are 5.1%, 1.9%, 3.1%, and 6.3%, respectively (Table 6). FIG. 2 illustrates GUS staining of transformed plants.

TABLE 6

Transformation frequencies of PMI selection of different cultivars

| Recipient name | Selectable marker | Number of explants (explant) | Number of positive plants (plant) | Transformation frequency (%) |
|---|---|---|---|---|
| Jack | *E. coli*PMI | 763 | 39 | 5.1% |
| Williams82 | *E. coli*PMI | 212 | 4 | 1.9% |
| ZH10 | *E. coli*PMI | 128 | 4 | 3.1% |
| ZH688 | *E. coli*PMI | 80 | 5 | 6.3% |

Example 13

Soybean genetic transformation using soybean-derived PMI gene (GmPMI-Glyma.18G296300.1) as a selectable marker:

1. Preparation of explant: Each mature seed of *Glycine max* 'Jack' was sterilized and then germinated on a solid medium for one day; two cotyledons and the first pair of true leaves were removed, and hypocotyl and meristem were preserved. Explants of meristems of soybean embryonic tips of *G. max* 'Jack' were obtained.

2. Preparation of infection suspension: 0.215 g of basic MS medium, 5 ml of 200×B5 vitamin, 30 g of sucrose, 1.0 mg of thidiazuron, and 1 g of 2-morpholinoethanesulfonic acid were dissolved in 1 L of water, and adjusted to pH 5.4 to obtain an infection medium.

Vector construction: An expression vector was constructed by using a binary vector pCAMBIA3301 as a basic transformation vector. A soybean-derived PMI gene (GmPMI-Glyma.18G296300.1, as shown in SEQ ID NO. 2) obtained on NCBI website was synthesized into a gene fragment and cloned into the binary vector pCAMBIA3301 to obtain a recombinant expression vector. There were two expression elements in the recombinant expression vector: one was a GUS expression element used for transient expression assay, i.e., pr35S-GUS-tNOS; the other was a selectable marker gene used for selection, i.e., pr35S-EcoliPMI-tNOS. The binary vector was introduced into *Agrobacterium* EHA101 by electroporation; after correct verification, recombinant *Agrobacterium* was obtained and stored in a refrigerator at −80° C. for use.

After culture, the recombinant *Agrobacterium* was dissolved in the infection medium; an infection suspension was obtained once OD$_{660}$ was measured to be 0.6.

3. Infection and co-culture: Explants of meristems of soybean embryonic tips were soaked in the infection suspension for 2 h; infected explants were removed, placed onto the surface of a co-culture medium or a piece of filter paper supplemented with 1 mL of liquid co-culture medium, and cultured in the dark at 23° C. for 5 days.

The co-culture medium was prepared as follows: 0.215 g of basic MS medium, 5 ml of 200×B5 vitamin, 30 g of sucrose, 1 g of 2-morpholinoethanesulfonic acid, and 7.5 g of agar were dissolved in 1 L of water, and adjusted to pH 5.6.

The liquid co-culture medium was prepared as follows: 0.215 g of basic MS medium, 5 ml of 200×B5 vitamin, 30 g of sucrose, and 1 g of 2-morpholinoethanesulfonic acid were dissolved in 1 L of water, and adjusted to pH 5.6.

4. Selective culture: The co-cultured explants were transferred onto a selective medium supplemented with mannose and cultured for three weeks at 25° C.; explants grown normally were selected as positive plants. The culture was on a 16 h light/8 h dark cycle. Light intensity was above 1,500 LUX.

The selective medium was prepared as follows: 0.31 g of basic B5 medium, 5 ml of 200×B5 vitamin, 5 g of sucrose, 20 g of mannose, 0.2 mg of thidiazuron, 1 g of 2-morpholinoethanesulfonic acid, and 7.5 g of agar were dissolved in 1 L of water, and adjusted to pH 5.6.

5. Shoot elongation: The selected positive plants were transferred onto a shoot elongation medium and kept culturing for three weeks to obtain elongated plants. Culture conditions were as follows: light culture at 25° C., on a 16 h light/8 h dark cycle. The light intensity was above 1,500 LUX.

The shoot elongation medium included: 0.31 g of basic B5 medium, 5 ml of 200×B5 vitamin, 5 g of sucrose, 20 g of mannose, 1 g of 2-morpholinoethanesulfonic acid, and 7.5 g of agar, at a pH of 5.6.

6. Transplantation and identification by staining: The elongated plants were identified by GUS staining; the stained elongated plants were directly transplanted in a culture matrix without rooting. The transplanted plants were watered and moisturized in plastic bags; one week later, plastic bags were removed and the plants were managed normally.

The culture matrix was a mixture of turfy soil and vermiculite in a volume ratio of 1:1. Culture conditions were: 28° C., a 16 h light/8 h dark cycle.

Identification by GUS staining: Leaves of elongated plants were placed in a GUS staining solution and allowed to stand for 12 h at 37° C. Leaves were removed and destained with 70% alcohol, and then leaf color was observed. Blue-stained leaves were transgenic positive plants.

Preparation of GUS staining solution was as follows: 25 ml of 1 M sodium phosphate ($Na_2PO_4$), ml of 500 mM sodium ethylenediamine tetracetate (EDTA), and 125 mg of 5-bromo-4-chloro-3-indolyl β-D-glucoside (X-Glu) were dissolved in water, and a the solution was adjusted to pH 8.0.

The foregoing test was done in triplicate. Numbers of explants and regenerated positive plants were counted, and transformation frequency (transformation frequency=number of positive plants/number of explants× 100%) was calculated.

Results showed that two soybean-derived PMI genes could serve as selectable marker genes in the soybean genetic transformation, and transformation frequencies obtained were 4.8% and 5.5%, respectively (Table 7).

TABLE 7

The transformation frequency of the soybean-derived PMI gene in the soybean genetic transformation

| Vector | Recipient cultivar | Selectable marker | Number of explants | Number of positive plants | transformation frequency |
|---|---|---|---|---|---|
| GmPMI-Glyma.18G296300.1 | Jack | GmPMI | 269 | 13 | 4.8% |

Example 14

Soybean genetic transformation using soybean-derived PMI gene (GmPMI-Glyma.08G365900.1) as a selectable marker:

1. Preparation of explant: Each mature seed of *Glycine max* 'Jack' was sterilized and then germinated on a solid medium for one day; two cotyledons and the first pair of true leaves were removed, and hypocotyl and meristem were preserved. Explants of meristems of soybean embryonic tips of *G. max* 'Jack' were obtained.

2. Preparation of infection suspension: 0.215 g of basic MS medium, 5 ml of 200×B5 vitamin, 30 g of sucrose, 1.0 mg of thidiazuron, and 1 g of 2-morpholinoethanesulfonic acid were dissolved in 1 L of water, and adjusted to pH 5.4 to obtain an infection medium.

Vector construction: An expression vector was constructed by using a binary vector pCAMBIA3301 as a basic transformation vector. A soybean-derived PMI gene (GmPMI-Gyma.08G365900.1, as shown in SEQ ID NO. 3) obtained on NCBI website was synthesized into a gene fragment and cloned into the binary vector pCAMBIA3301 to obtain a recombinant expression vector. There were two expression elements in the recombinant expression vector: one was a GUS expression element used for transient expression assay, i.e., pr35S-GUS-tNOS; the other was a selectable marker gene used for selection, i.e., pr35S-EcoliPMI-tNOS. The binary vector was introduced into *Agrobacterium* EHA101 by electroporation; after correct verification, recombinant *Agrobacterium* was obtained and stored in a refrigerator at −80° C. for use.

After culture, the recombinant *Agrobacterium* was dissolved in the infection medium; an infection suspension was obtained once $OD_{660}$ was measured to be 0.6.

3. Infection and co-culture: Explants of meristems of soybean embryonic tips were soaked in the infection suspension for 2 h; infected explants were removed, placed onto the surface of a co-culture medium or a piece of filter paper supplemented with 1 mL of liquid co-culture medium, and cultured in the dark at 23° C. for 5 days.

The co-culture medium was prepared as follows: 0.215 g of basic MS medium, 5 ml of 200×B5 vitamin, 30 g of sucrose, 1 g of 2-morpholinoethanesulfonic acid, and 7.5 g of agar were dissolved in 1 L of water, and adjusted to pH 5.6.

The liquid co-culture medium was prepared as follows: 0.215 g of basic MS medium, 5 ml of 200×B5 vitamin, 30 g of sucrose, and 1 g of 2-morpholinoethanesulfonic acid were dissolved in 1 L of water, and adjusted to pH 5.6.

4. Selective culture: The co-cultured explants were transferred onto a selective medium supplemented with mannose and cultured for three weeks at 25° C.; explants grown normally were selected as positive plants. The culture was on a 16 h light/8 h dark cycle. Light intensity was above 1,500 LUX.

The selective medium was prepared as follows: 0.31 g of basic B5 medium, 5 ml of 200×B5 vitamin, 5 g of sucrose, 20 g of mannose, 0.2 mg of thidiazuron, 1 g of 2-morpholinoethanesulfonic acid, and 7.5 g of agar were dissolved in 1 L of water, and adjusted to pH 5.6.

5. Shoot elongation: The selected positive plants were transferred onto a shoot elongation medium and kept culturing for three weeks to obtain elongated plants. Culture conditions were as follows: light culture at 25° C., on a 16 h light/8 h dark cycle. The light intensity was above 1,500 LUX.

The shoot elongation medium included: 0.31 g of basic B5 medium, 5 ml of 200×B5 vitamin, 5 g of sucrose, 20 g of mannose, 1 g of 2-morpholinoethanesulfonic acid, and 7.5 g of agar, at a pH of 5.6.

6. Transplantation and identification by staining: The elongated plants were identified by GUS staining; the stained elongated plants were directly transplanted in a culture matrix without rooting. The transplanted plants were watered and moisturized in plastic bags; one week later, plastic bags were removed and the plants were managed normally.

The culture matrix was a mixture of turfy soil and vermiculite in a volume ratio of 1:1. Culture conditions were: 28° C., a 16 h light/8 h dark cycle.

Identification by GUS staining: Leaves of elongated plants were placed in a GUS staining solution and allowed to stand for 12 h at 37° C. Leaves were removed and destained with 70% alcohol, and then leaf color was observed. Blue-stained leaves were transgenic positive plants.

Preparation of GUS staining solution was as follows: 25 ml of 1 M sodium phosphate (Na$_2$PO$_4$), ml of 500 mM sodium ethylenediamine tetracetate (EDTA), and 125 mg of 5-bromo-4-chloro-3-indolyl β-D-glucoside (X-Glu) were dissolved in water, and the solution was adjusted to pH 8.0.

The foregoing test was done in triplicate. Numbers of explants and regenerated positive plants were counted, and transformation frequency (transformation frequency=number of positive plants/number of explants× 100%) was calculated.

Results showed that two soybean-derived PMI genes could serve as selectable marker genes in the soybean genetic transformation, and the transformation frequency obtained was 5.5% (Table 8).

TABLE 8

The transformation frequency of the soybean-derived PMI gene in the soybean genetic transformation

| Vector | Recipient cultivar | Selectable marker | Number of explants | Number of positive plants | transformation frequency |
|---|---|---|---|---|---|
| GmPMI-Glyma.08G365900.1 | Jack | GmPMI | 309 | 17 | 5.5% |

The above descriptions are merely preferred implementations of the present invention. It should be noted that a person of ordinary skill in the art may further make several improvements and modifications without departing from the principle of the present invention, but such improvements and modifications shall also be deemed as falling within the protection scope of the present invention.

What is claimed is:

1. A soybean genetic transformation method using PMI as selectable gene, consisting of the following steps:

A, soaking soybean explants in a recombinant *Agrobacterium*-containing infection suspension to obtain infected explants;

a PMI gene and a target gene being present in the recombinant *Agrobacterium*; the infection suspension, apart from the recombinant *Agrobacterium*, further comprising an infection medium, wherein the infection medium uses MS as a basic medium and further comprises 1.0 to 2.0 mg/L thidiazuron;

B. co-culturing the infected explants to obtain co-cultured explants;

a medium for the co-culture is consisted of MS, B5 vitamin, sucrose, 2-morpholinoethanesulfonic acid, and agar, at a pH of 5.4 to 5.8; the medium for the co-culture uses the MS as a basic medium;

C. culturing the co-cultured explants on a selective medium directly for 18 to 25 days, to select positive plants without growth inhibition;

the selective medium using mannose as a selective agent; and

D. conducting shoot elongation and transplantation on the positive plants;

wherein, in the step C, the selective medium uses B5 as a basic medium and further comprises B5 vitamin, sucrose, mannose, thidiazuron, 2-morpholinoethanesulfonic acid, and agar, at a pH of 5.4 to 5.8;

and the culturing conditions in the step C comprise: culture temperature 25 to 28° C., and illumination time 14 to 18 h/day.

2. The soybean genetic transformation method according to claim 1, wherein, in the step A, the soybean explants comprise explants of meristems of soybean embryonic tips or soybean calluses; preferred cultivars of the soybean explants comprise *Glycine max* 'Jack', *G. max* 'William82', *G. max* 'Zhonghuang 10', or *G. max* 'Zhonghuang, 688'.

3. The soybean genetic transformation method according to claim 1, wherein, in the step A, the infection medium uses MS as a basic medium and further comprises B5 vitamin, sucrose, thidiazuron, and 2-morpholinoethanesulfonic acid.

4. The soybean genetic transformation method according to claim 2, wherein, in the step A, the infection medium uses MS as a basic medium and further comprises thidiazuron.

5. The soybean genetic transformation method according to claim 1, wherein, in the step A, the PMI gene comes from microbes or plants; the microbes comprise *Escherichia coli*; the plants comprise soybean, rice, or corn.

6. The soybean genetic transformation method according to claim 1, wherein, in the step B, conditions of the co-culture comprise: culture temperature 19 to 24° C., and illumination time 0 to 18 h/day.

7. The soybean genetic transformation method according to claim 1, wherein, in the step D, a medium for the shoot elongation uses B5 as a basic medium and further comprises B5 vitamin, sucrose, mannose, 2-morpholinoethanesulfonic acid, and agar, at a pH of 5.4 to 5.8.

8. The soybean genetic transformation method according to claim 1, wherein, in the step D, conditions of the shoot elongation comprise: culture temperature 25 to 28° C., and illumination time 14 to 18 h/day.

9. The soybean genetic transformation method according to claim 2, wherein, in the step A, the PMI gene comes from microbes or plants; the microbes comprise *Escherichia coli*; the plants comprise soybean, rice, or corn.

10. The soybean genetic transformation method according to claim 1, wherein, in the step B, conditions of the co-culture comprise: culture temperature 19 to 24° C., and illumination time 0 to 18 h/day.

11. The soybean genetic transformation method according to claim 7, wherein, in the step D, conditions of the shoot elongation comprise: culture temperature 25 to 28° C., and illumination time 14 to 18 h/day.

* * * * *